(12) United States Patent
Zhao et al.

(10) Patent No.: US 7,393,953 B2
(45) Date of Patent: Jul. 1, 2008

(54) POLYMERIC ACYL DERIVATIVES OF INDOLES

(75) Inventors: Hong Zhao, Edison, NJ (US); Richard B. Greenwald, Somerset, NJ (US)

(73) Assignee: Enzon, Inc., Bridgewater, NJ (US)

( * ) Notice: Subject to any disclaimer, the term of this patent is extended or adjusted under 35 U.S.C. 154(b) by 582 days.

(21) Appl. No.: 10/403,789

(22) Filed: Mar. 31, 2003

(65) Prior Publication Data

US 2003/0202959 A1 Oct. 30, 2003

Related U.S. Application Data

(60) Provisional application No. 60/369,732, filed on Apr. 4, 2002.

(51) Int. Cl.
C07D 487/04 (2006.01)
(52) U.S. Cl. ....................................... 540/520
(58) Field of Classification Search ................. 540/520; 514/212.06
See application file for complete search history.

(56) References Cited

FOREIGN PATENT DOCUMENTS

WO    WO 99/65910    12/1999

OTHER PUBLICATIONS

Maryse Leost, et al. Paullones are potent inhibitors of glycogen . . . Eur. J. Biochem. 267, 5983-5994 (2000) c FEBS 2000 pp. 5983-5994.
Conrad Kunick, et al. 2-Substituted Paullones: CDK1/Cyclin B-Inhibiting Property . . . Bioorganic & Medicinal Chemistry Letters 10 (2000) 567-569.
Daniel W. Zaharevitz, et al. Discovery and Intitial Characterization of Paullones . . . Cancer Research 59, 2566-2569, Jun. 1, 1999.
Christiane Schultz, et al. Paullones, a Seriers of Cyclin-Dependent Kinase Inhibitors . . . J. Med. Chem. 1999, 42, 2909-2919.

*Primary Examiner*—Bruck Kifle
(74) *Attorney, Agent, or Firm*—Lucas & Mercanti, LLP

(57) ABSTRACT

Polymeric derivatives of indoles such as

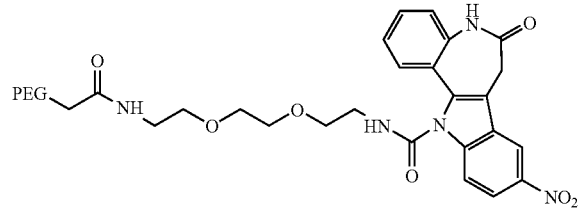

are disclosed. Methods of making and using the same as well as related polymeric conjugates are also disclosed.

14 Claims, 2 Drawing Sheets

POLYMERIC ACYL DERIVATIVES OF INDOLES

CROSS REFERENCE TO RELATED APPLICATION

This application claims the benefit of priority from U.S. provisional patent application No. 60/369,732, filed Apr. 4, 2002, the contents of which are incorporated herein by reference.

OBJECT

This application relates to novel indole derivatives useful in the treatment of proliferative diseases. In particular, the invention relates to polymeric acyl derivatives of indoles such as paullones having increased solubility and methods of preparing the same.

BACKGROUND

It has been found that a family of protein kinases, namely cyclin-dependent kinases or CDKs, play a central role in the cell division cycle. Deregulation of CDK activity has been documented in a number of human primary tumors and tumor cell lines, see Kamb, A. *Cyclin-dependent kinase inhibitors and human cancer,* Curr. Top. Microbiol. Immunol., 227: 139-148, 1998. It stands to reason therefore that preferential inhibition of these kinases would be key in the treatment or prevention of proliferative diseases.

Paullones represent a novel class of small molecule CDK inhibitors. They are a family of benzazepinones with promising antitumoral properties. Recently, paullones have been described as potent ATP-competitive inhibitors of the cell cycle regulating cyclin-dependent kinases. They are also indicated as potent inhibitors of glycogen synthase kinase-3B (GSK-3B) and the neuronal DCK5/p25, see Leost et al., *Paullones are potent inhibitors of glycogen synthase kinase-3B and cyclin-dependent kinase 5/p25*, Eur. J. Biochem., 267: 5983-5994, 2000.

Several chemical agents that are selective CDK inhibitors are known or have been developed such as lactones (e.g. butyrolactone I), flavonoids (e.g. flavopiridol) and purine derivatives to name a few. Some have shown antiproliferative activity for colon and pancreatic carcinoma cell lines. Flavopiridol has entered clinical trials as an anticancer agent. Paullones have been compared to these known compounds and have been found to be equipotent with respect to CDK inhibition.

One lead stucture alsterpaullone (9-nitro-7,12-dihydroindolo-[3,2-d][1]benzazepin-6(5H)-one, has been derivatized at both the lactam and/or indole portion in an effort to increase anti-tumor activity. Although the CDK inhibition activity remains high, the antiproliferative activity remains poor throughout the paullone family. One explanation could be the insolubility of these compounds.

Over the years, several methods of administering biologically-effective materials to mammals have been proposed. Many medicinal agents are available as water-soluble salts and can be included in pharmaceutical formulations relatively easily. Problems arise when the desired medicinal agent is either insoluble in aqueous fluids or is rapidly degraded in vivo. Paullones are often especially difficult to solubilize.

One way to solubilize medicinal agents is to include them as part of a soluble prodrug. Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols. See Remington's Pharmaceutical Sciences, 16$^{th}$ Ed., A. Osol, Ed. (1980), the disclosure of which is incorporated by reference herein.

Prodrugs are biologically inert or substantially inactive forms of the parent or active compound. The rate of release of the active drug, i.e. the rate of hydrolysis, is influenced by several factors but especially by the type of bond joining the parent drug to the modifier. Care must be taken to avoid preparing prodrugs which are eliminated through the kidney or reticular endothelial system, etc. before a sufficient amount of hydrolysis of the parent compound occurs.

Incorporating a polymer as part of a prodrug system has been suggested to increase the circulating life of a drug. However, it has been determined that when only one or two polymers of less than about 10,000 daltons are conjugated to certain biologically active substances such as alkaloid compounds, the resulting conjugates are rapidly eliminated in vivo, especially if a somewhat hydrolysis-resistant linkage is used. In fact, such conjugates can be so rapidly cleared from the body that even if a hydrolysis-prone ester linkage is used, not enough of the parent molecule is regenerated in vivo to be therapeutic.

Paullones are often poorly water soluble and are examples of substances which would benefit from PEG prodrug technology.

Attempts to increase the antiproliferative activity of the paullones has been reported. See Kunick et al., *2-Substituted Paullones. CDK1/Cyclin B-Inhibiting Property and In Vitro Antiproliferative Activity,* Bioorganic & Medicinal Chemistry Letters, 10: 567-569, 2000. However, the study concentrates on substitution at the 2 position of 9-trifluoromethyl-paullones specifically with groups such as cyano, and carbon chain esters and ethers of varying length and saturation. The study does not solve the problem of maintaining CDK activity while increasing antiproliferative activity or improving the solubility of paullone analogs.

Thus, there still exists a need for derivatized heteroaromatic amine-containing compounds, for example, indole-containing compounds such as paullones, that exhibit potent preferential CDK inhibition combined with high antiproliferative activity. The present invention addresses this need.

SUMMARY OF THE INVENTION

In one aspect of the invention, compounds of Formula (I) are provided:

(I)

wherein:
$R_1$ is a polymeric residue;
$Y_1$ is O, S or $NR_2$;
$R_2$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$heteroalkyls, substituted $C_{1-6}$heteroalkyls, $C_{1-6}$alkoxy, phenoxy and $C_{1-6}$heteroalkoxy;

$L_1$ is a bifunctional linker;

p is 0 or 1 and

B is a residue of a heteroaromatic amine-containing moiety such as, biologically active moieties containing indoles or related compounds capable of undergoing the acylation reactions described herein.

Another aspect of the invention includes bifunctional compounds that are formed when the polymeric residue ($R_1$) includes both an alpha and an omega terminal linking group so that two equivalents of the heteroaromatic amine-containing moiety such as a biologically active agent, drug or protein, designated herein as B, is delivered. An example of such a bifunctional polymer conjugate is illustrated below as formula (II):

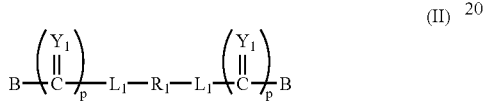
(II)

wherein all variables are as described above.

For purposes of the present invention, the term "residue" shall be understood to mean that portion of the heteroaromatic amine-containing biologically active compound, preferably an indole-containing compound, which remains after it has undergone a substitution reaction in which the polymeric prodrug carrier portion has been attached via acylation of the indole secondary amine.

For purposes of the present invention, the term "polymeric residue" or "PEG residue" shall each be understood to mean that portion of the polymer or PEG which remains after it has undergone a reaction with a heteroaromatic amine-containing compound.

For purposes of the present invention, the term "alkyl" shall be understood to include straight, branched, substituted, e.g. halo-, alkoxy-, nitro-, $C_{1-12}$alkyls, $C_{3-8}$cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo- shall be understood to include fluoro, chloro, iodo and bromo.

The term "sufficient amounts" for purposes of the present invention shall mean an amount which achieves a therapeutic effect as such effect is understood by those of ordinary skill in the art.

One advantage of the invention is that the target compound delivered via the polymeric transport system demonstrates an increase in solubility.

Another advantage of the compounds of the invention is that in certain preferred embodiments, the polymeric prodrug platform can be releasably attached to heteroaromatic amine groups found on various biologically useful small molecules, peptides and the like. It was not previously known that such biologically active moieties could be functionalized at this position without losing bioactivity.

A further advantage of the compounds of this invention is that they can be substituted with various moieties between the polymeric residue and attached bioeffective agent that can effect the rate of hydrolysis of the prodrug. The artisan thus has the ability to include substituents that allow for modulation of the rate of hydrolysis of the prodrug.

Methods of making and using the compounds and conjugates described herein are also provided.

DETAILED DESCRIPTION OF THE INVENTION

A. Formula (I)

Figure 1:
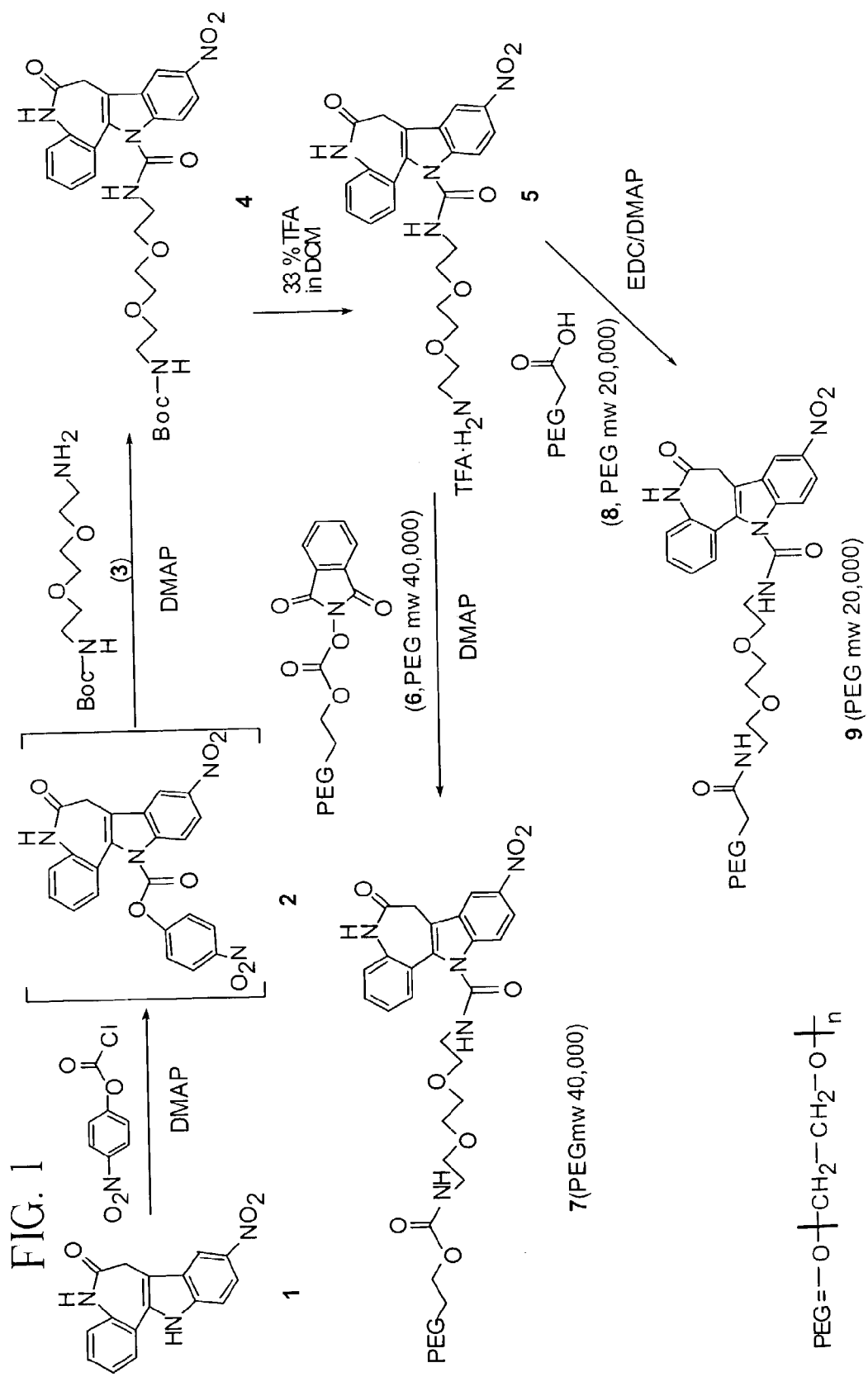
FIGS. 1 and 2 schematically illustrate methods of forming compounds of the present invention which are described in the Examples.

In one preferred embodiment of the invention, there are provided compounds of the formula:

(I)

wherein:

$R_1$ is a polymeric residue;

$Y_1$ is O, S or $NR_2$;

$R_2$ is selected from the group consisting of hydrogen, $C_{1-6}$alkyls, $C_{3-12}$branched alkyls, $C_{3-8}$cycloalkyls, $C_{1-6}$substituted alkyls, $C_{3-8}$substituted cyloalkyls, aryls, substituted aryls, aralkyls, $C_{1-6}$heteroalkyls, substituted $C_{1-6}$heteroalkyls, $C_{1-6}$alkoxy, phenoxy and $C_{1-6}$heteroalkoxy;

$L_1$ is a bifunctional linker;

p is 0 or 1 and

B is a residue of a heteroaromatic amine-containing compound.

The polymer transport system of the present invention is based in large part on the polymeric residue designated herein as $R_1$. Optionally, $R_1$ includes a capping group A. The polymer capping group A includes moieties such as OH, $CO_2H$, $NH_2$, SH, $C_{1-6}$alkyl moieties, and compounds of formula (III) shown below,

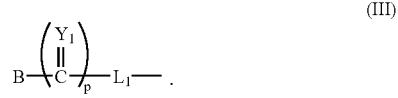
(III)

The preferred capping group (III) allows compositions of formula (II) shown below to be formed:

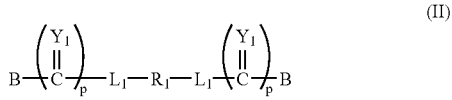
(II)

wherein all variables are as previously described.

With regard to the other variables which comprise the formula of the present invention, the following are preferred:

$Y_1$ is oxygen;

$R_2$ is selected from hydrogen and $C_{1-6}$alkyl, with methyl and ethyl being most preferred;

$L_1$ is selected from among one of the following non-limiting compounds:

—NH(CH$_2$CH$_2$O)$_n$(CH$_2$)$_n$NR$_3$—,

—NH(CH$_2$CH$_2$O)$_n$C(O)—,

—NH(CR$_4$R$_5$)$_n$OC(O)—,

—C(O)(CR$_4$R$_5$)$_n$NHC(O)(CR$_8$R$_7$)$_q$NR$_3$—,

—C(O)O(CH$_2$)$_n$O—,

—C(O)(CR$_4$R$_5$)$_n$NR$_3$—,

—C(O)NH(CH$_2$CH$_2$O)$_n$(CH$_2$)$_n$NR$_3$—,

—C(O)O—(CH$_2$CH$_2$O)$_n$NR$_3$—,

—C(O)NH(CR$_4$R$_5$)$_n$O—,

—C(O)O(CR$_4$R$_5$)$_n$O—,

—C(O)NH(CH$_2$CH$_2$O)$_n$—,

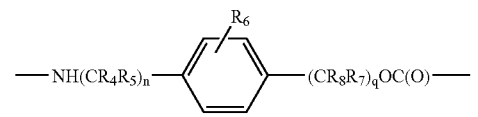
and
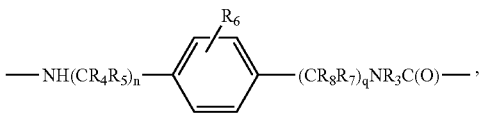, wherein
$R_3$, $R_4$, $R_5$, $R_7$ and $R_8$ are independently selected from the same group as that which defines $R_2$ above;
$R_6$ is selected from the group consisting of that which defines $R_2$, NO$_2$, haloalkyl and halogen; and
n and q are each a positive integer.

Drug Generation Via Hydrolysis of the Prodrug

Preferably the linkages included in the compounds have hydrolysis rates in the plasma of the mammal being treated which are short enough to allow sufficient amounts of the parent compounds, i.e. the heteroaromatic amine containing bioactive compound, to be released prior to elimination.

Substantially Non-Antigenic Polymers

As stated above, $R_1$ is a water soluble polymeric residue which is preferably substantially non-antigenic such as polyalkylene oxide or polyethylene glycol. In preferred aspects of the invention, $R_1$ further includes the previously mentioned capping group, designated A, which allows a bifunctional or bis-polymer system to be formed.

As an example, the polyethylene glycol residue portion of the inventive compounds can be selected from the following non-limiting list:

A—O—(CH$_2$CH$_2$O)$_x$—

A—O—(CH$_2$CH$_2$O)$_x$—CH$_2$C(O)—O—,

A—O—(CH$_2$CH$_2$O)$_x$—CH$_2$CH$_2$NR$_3$—,

A—O—(CH$_2$CH$_2$O)$_x$—CH$_2$CH$_2$SH,

—O—C(O)CH$_2$—O—(CH$_2$CH$_2$O)$_x$—CH$_2$C(O)—O—,

—NR$_3$CH$_2$CH$_2$—O—(CH$_2$CH$_2$O)$_x$—CH$_2$CH$_2$NR$_3$—,

—SHCH$_2$CH$_2$—O—(CH$_2$CH$_2$O)$_x$—CH$_2$CH$_2$SH—, wherein x is the degree of polymerization,
$R_3$ is as described herein above and
A is a capping group.

For the purpose of the present invention the structure:

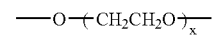

wherein x is a positive integer, is referred to as PEG throughout the application.

The degree of polymerization for the polymer (x) can be from about 10 to about 2,300. This represents the number of repeating units in the polymer chain and is dependent on the molecular weight of the polymer. The (A) moiety is a capping group as defined herein, i.e. a group which is found on the terminal of the polymer and, in some aspects, can be selected from any of NH$_2$, OH, SH, CO$_2$H, C$_{1-6}$alkyls or other PEG terminal activating groups, as such groups are understood by those of ordinary skill.

Also useful are polypropylene glycols, branched PEG derivatives such as those described in commonly-assigned U.S. Pat. No. 5,643,575, "star-PEG's" and multi-armed PEG's such as those described in Shearwater Corporation's 2001 catalog "Polyethylene Glycol and Derivatives for Biomedical Application". The disclosure of each of the foregoing is incorporated herein by reference. It will be understood that the water-soluble polymer can be functionalized for attachment to the bifunctional linkage groups if required without undue experimentation.

In many aspects of the present invention, bis-activated polyethylene glycols are preferred when di- or multi-substituted polymer conjugates are desired. Alternatively, polyethylene glycols (PEG's), mono-activated, C$_{1-4}$alkyl-terminated polyalkylene oxides (PAO's) such as mono-methyl-terminated polyethylene glycols (mPEG's) are preferred when mono-substituted polymers are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting CH$_3$O-PEG-OH (mPEG-OH) to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in average molecular weight, the polymer portion of the prodrug is at least about 20,000 Da average in most aspects of the invention. Preferably, $R_1$ has a weight average molecular weight of from about 20,000 Da to about 100,000 Da and more preferably from about 25,000 Da to about 60,000 Da. The average molecular weight of the polymer selected for inclusion in the prodrug must be sufficient so as to provide sufficient circulation of the prodrug before hydrolysis of the linker.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO-based polymers, $R_1$ is optionally selected from among one or more effectively non-antigenic materials such as dextran, polyvinyl alcohols, carbohydrate-based polymers, hydroxypropylmeth-acrylamide (HPMA), polyalkylene oxides, and/or copolymers thereof. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals.

It will be clear from the foregoing that other polyalkylene oxide derivatives of the foregoing, such as the polypropylene glycol acids, etc., as well as other bifunctional linking groups are also contemplated.

Residues of Heteroaromatic Amine-Containing Compounds

In some aspects of the invention, B is preferably a residue of a heteroaromatic amine-containing compound, preferably an indole-containing compound. A non-limiting list of suitable compounds includes residues of organic compounds, enzymes, proteins, polypeptides, etc. Some preferred organic compounds include, without limitation, CDK inhibitors such as the paullone structures are shown below

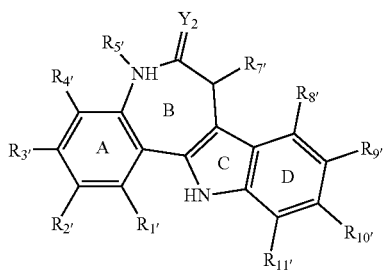

wherein:
$Y_2$ is O, S or $NR_{12'}$;
$R_{1'}$—$R_{12'}$ are each independently selected from the group consisting of hydrogen, $C_{1-6}$alkyls, $C_{3-12}$branched alkyls, $C_{3-8}$cycloalkyls, $C_{1-6}$substituted alkyls, $C_{3-12}$alkenyls, $C_{3-12}$substituted alkenyls, $C_{3-12}$alkynyls, $C_{3-12}$substituted alkynyls, $C_{3-8}$substituted cycloalkyls, aryls, substituted aryls, aralkyls, $C_{1-6}$hetero-alkyls, substituted $C_{1-6}$heteroalkyls, $C_{1-6}$alkoxy, phenoxy, $C_{1-6}$heteroalkoxy, halo-, nitro-, cyano-, hydroxy-, amino-, carboxy- and trifluormethyl, etc.

More specifically substituted paullones such as, for example,

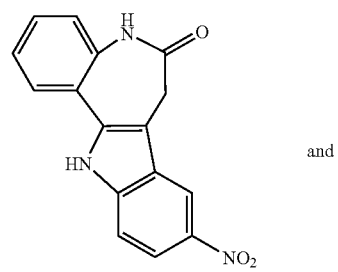

and alsterpaullone

kenpaullone are preferred.

Other CDK inhibitors useful in the methods of the invention include:

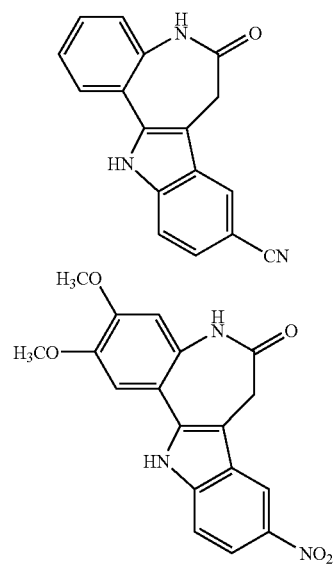

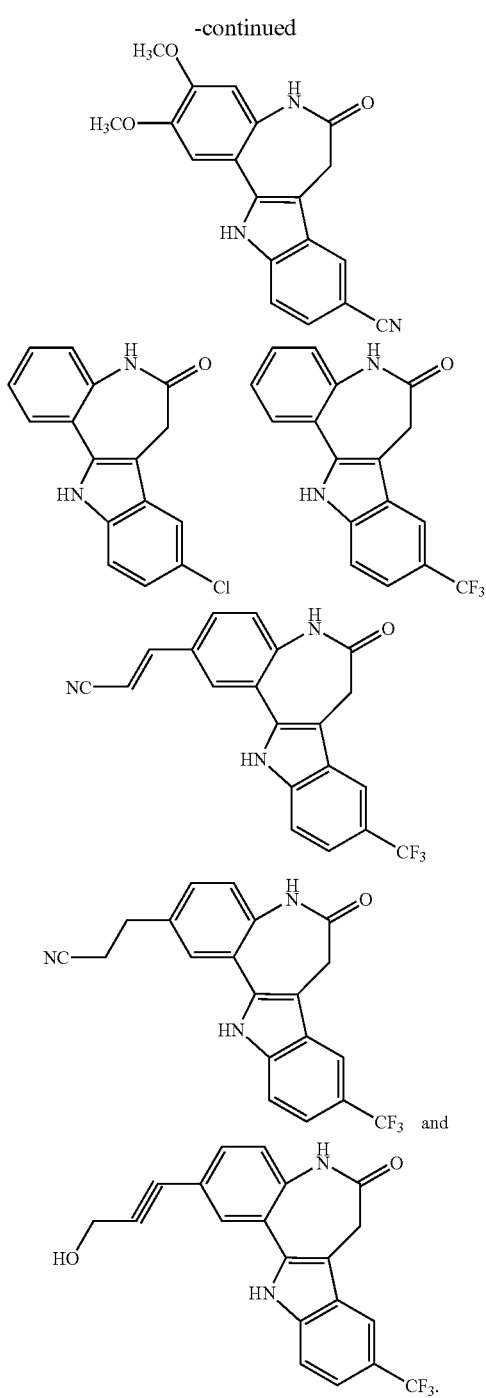

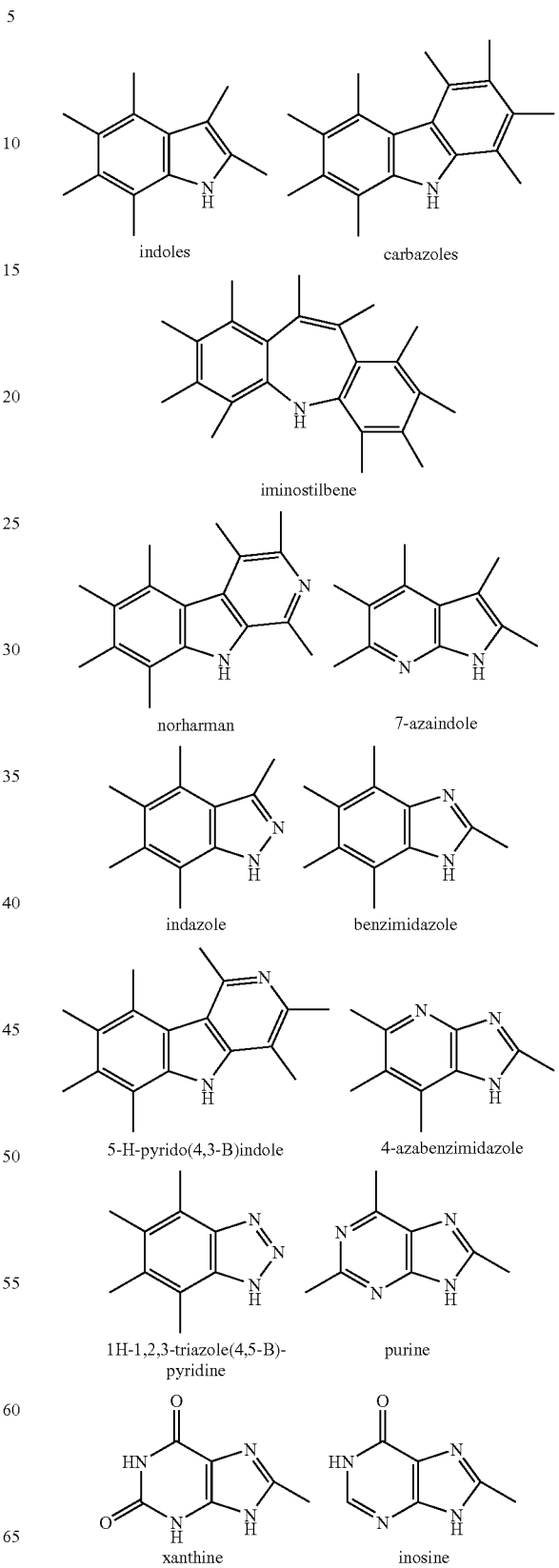

Other known derivatives of the paullone family such as those found in Leost et al., *Paullones Are Potent Ihnhibitors of Glycogen Synthase Kinase-3B and Cyclin-dependent Kinase 5/p25*, Eur. J. Biochem, (2000), 267, 5983-5994, and PCT application WO 99/65910 filed Jun. 16, 1999, are contemplated as suitable compounds for the purpose of the present invention. The disclosures of each of the foregoing are incorporated by reference herein. Paullones have antitumor activity in cancers such as leukimia, non-small cell lung cancers, central nervous system cancers, melanomas, ovarian cancers, renal cancers prostate cancers and breat cancers.

In addition, other compounds contemplated as suitable for the methods of the invention include those having the general structures shown below:

-continued

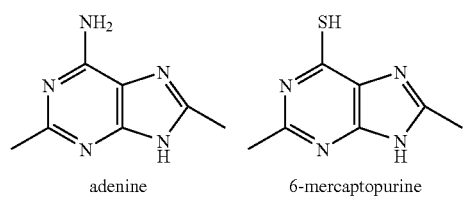

adenine      6-mercaptopurine

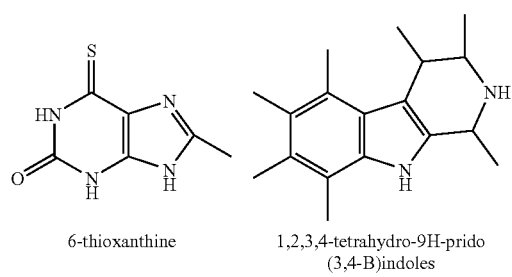

6-thioxanthine      1,2,3,4-tetrahydro-9H-prido (3,4-B)indoles

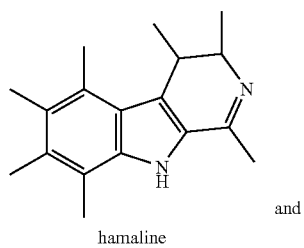

and hamaline

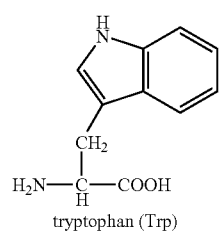

tryptophan (Trp)

wherein the straight lines indicate possible points of substitution.

Examples of biologically active compounds containing indole or indole-like moieties include but are not limited to:
anticancer agents such as

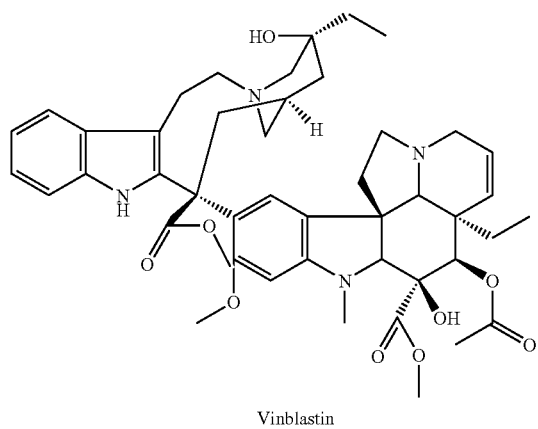

Vinblastin

-continued
and

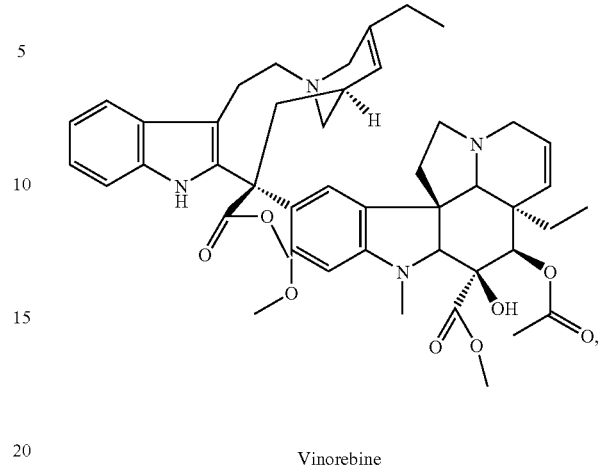

Vinorebine vasodilator, β-adrenergic blocking agents such as

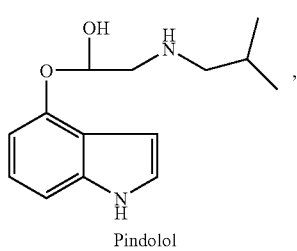

Pindolol

α2 adrenergic antagonists such as

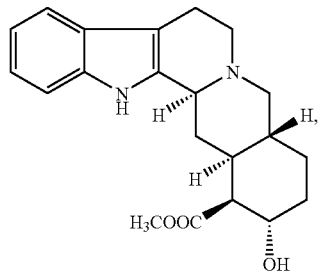

Yohimbine mixed dopamine agonists/antagonists such as

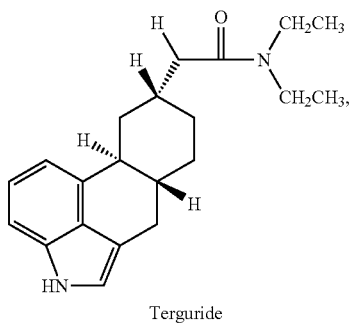

Terguride calcium channel blockers such as

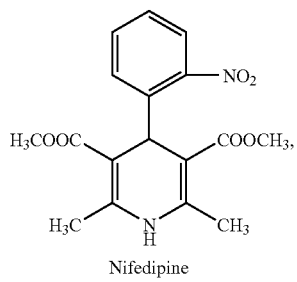
Nifedipine broad range serotonergic, dopaminiergic and α-adrenergic active compounds such as

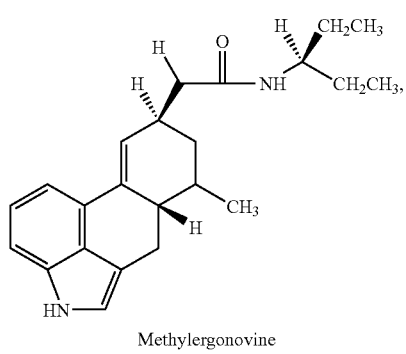
Methylergonovine serotonin precursors, antidepressants such as

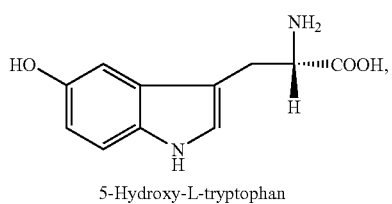
5-Hydroxy-L-tryptophan potent 5-HT1c serotonin receptor antagonists such as

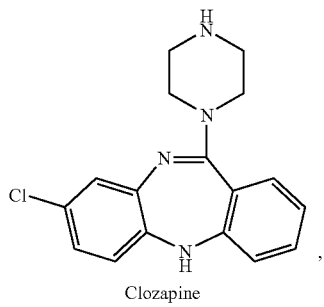
Clozapine highly selective, non-peptide δ-opioid antagonists such as

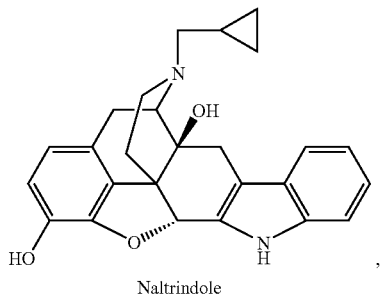
Naltrindole antihypertensive agents such as,

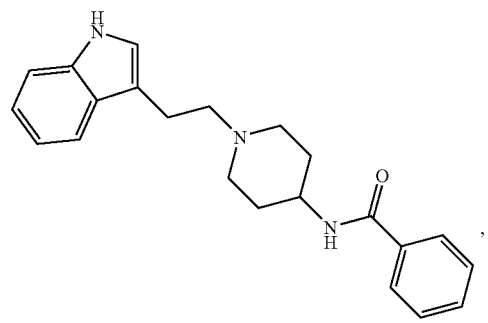
Indoramin plant growth regulating agents such as

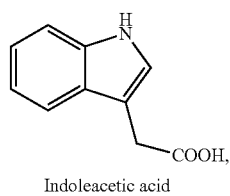
Indoleacetic acid highly selective κ-opioid antagonists such as

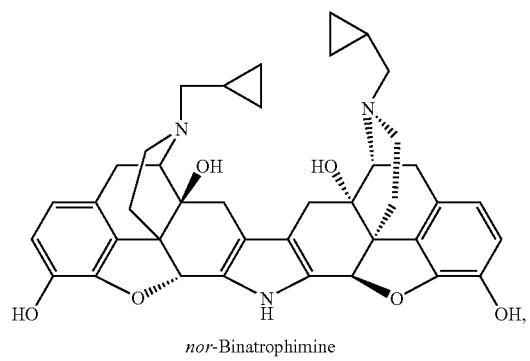
nor-Binatrophimine and others selected from anthracycline compounds and related anti-metabolite compounds. Alternatively, other suitable compounds contemplated as useful in the methods of the invention can be residues of amine-containing cardiovascular agents, anti-neoplastic agents, anti-infective agents, anti-fungal agents, anti-anxiety agents, gastrointestinal agents, central nervous system-activating agents, analgesic agents, fertility agents, contraceptive agents, anti-inflammatory agents, steroidal agents, anti-urecemic agents, vasodilating agents, and vasoconstricting agents.

Those of ordinary skill in the art will realize that certain biologically active compounds contain multiple functional groups, some of which must be protected or blocked first before the methods of this invention can be applied to such compounds.

In a preferred aspect of the invention, the heteroaromatic amine-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds can be similarly modified without undue experimentation. It is to be understood that those biologically active materials not specifically mentioned but having suitable heteroaromatic amine groups are also intended and are within the scope of the present invention. The only limitations on the types of heteroaromatic-amine containing molecules suitable for inclusion herein is that there is available at least one amine moiety capable of taking on aromatic characteristics which can react and link with a carrier portion and that there is not substantial loss of bioactivity after the prodrug system releases and regenerates the parent compound.

It is noted that parent compounds suitable for incorporation into the prodrug compositions of the invention, may themselves be substances/compounds which are not active after hydrolytic release from the linked composition, but which will become active after undergoing a further chemical process/reaction. For example, an anticancer drug that is delivered to the bloodstream by the double prodrug transport system, may remain inactive until entering a cancer or tumor cell, whereupon it is activated by the cancer or tumor cell chemistry, e.g., by an enzymatic reaction unique to that cell.

Synthesis of the Polymeric Prodrug Transport System

Synthesis of specific representative polymer prodrugs is set forth in the Examples. Generally, however, in one preferred method of preparing the prodrug transport systems of the present invention, the indole of the biologically active material or parent molecule to be delivered by the transport system is first acylated under basic conditions. Once activated, a blocked bifunctional spacer is attached, deblocked and reacted with an activated polymer such as SC-PEG or PEG-COOH. In FIG. 1, the indole ring of the paullone is activated by reacting the substrate with an acylating agent under basic conditions. Once activated, the intermediate is then reacted with a protected bifunctional linker. After deprotection, the polymer residue is coupled to the linker-paullone moiety under basic coupling conditions to form the desired product.

A non-limiting list of acylating agents include phosgene, triphosgene, disuccinimidyl carbonate, carbonyl diimidazole, para-nitrophenyl chloroformate, N-chlorocarbonyloxyphthalimide and diphthalimido carbonate.

Figure 2:
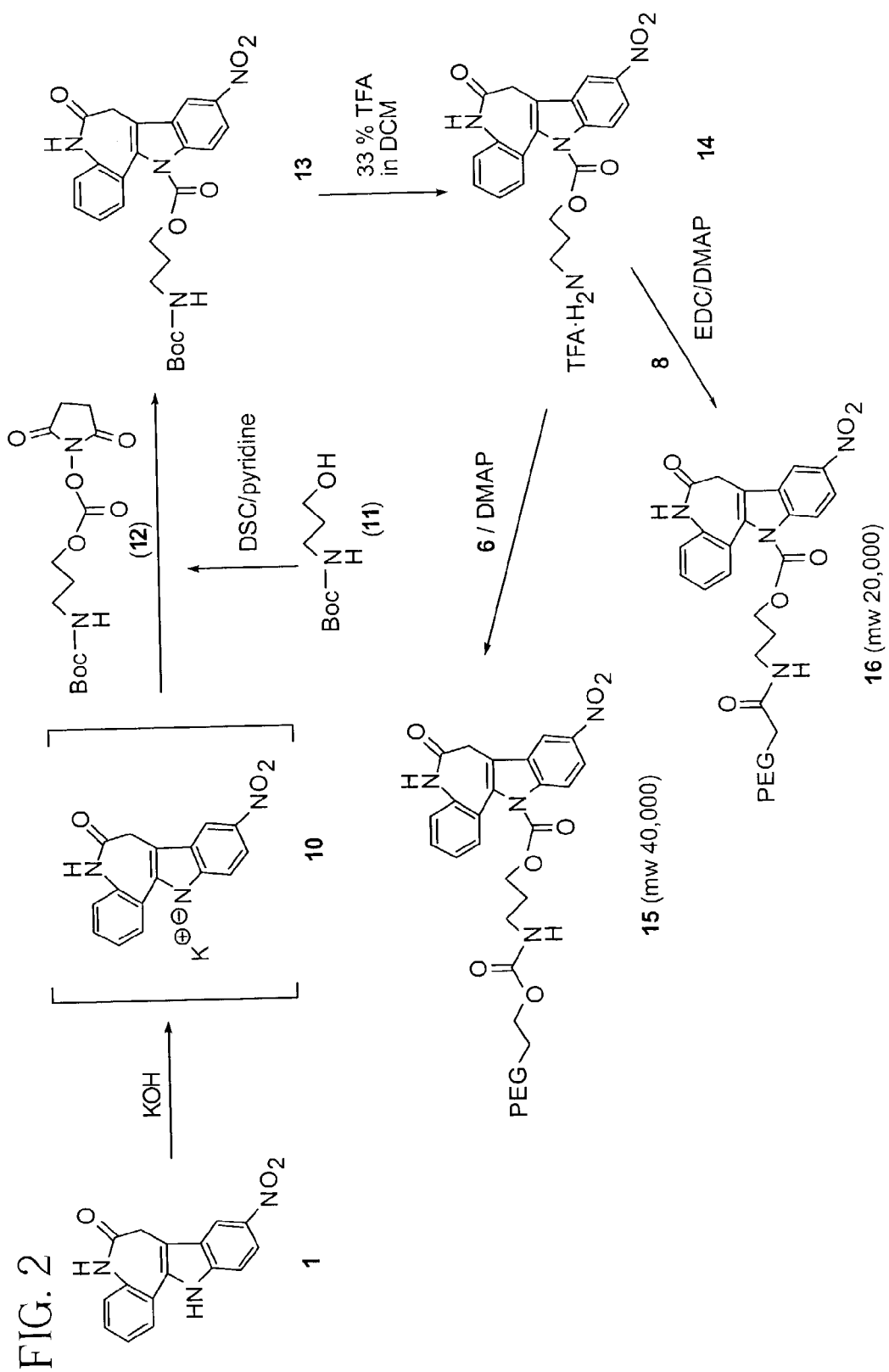

Alternatively, as shown in FIG. 2, the indole-containing compound is initially treated with a strong base such as, for example, KOH or potassium t-butoxide, and the indole nitrogen of the paullone is deprotonated. The intermediate is then reacted with an amine-protected bifunctional acid chloride. The product is then deprotected with acid and reacted with an activated polymer to attach a polymeric residue under basic coupling conditions and form the desired product.

A non-limiting list of activated polymers include bis-succinimidyl carbonate activated PEG (SC-PEG), bis-thiazolidine-2-thione activated PEG (T-PEG), N-hydroxyphthalamidyl carbonateactivated PEG (BSC-PEG), (see commonly assigned U.S. Ser. No. 09/823,296, the disclosure of which is incorporated herein by reference), succinimidyl succinate activated PEG (SS-PEG) and mono-activated PEG's such as those found in, for example, in the aforementioned 2001 Shearwater Catalog.

Conjugation of the intermediate to the PEG residue can be carried out in the presence of a coupling agent. A non-limiting list of suitable coupling agents include 1,3-diisopropylcarbodiimide (DIPC), any suitable dialkyl carbodiimide, 2-halo-1-alkyl-pyridinium halides (Mukaiyama reagents), 1-(3-dimethylamino-propyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably the substituents are reacted in an inert solvent such as tetrahydrofuran (THF), acetonitrile ($CH_3CN$), methylene chloride (DCM), chloroform ($CHCl_3$), dimethyl formamide (DMF) or mixtures thereof. The reaction is preferably conducted in the presence of a base, such as dimethylaminopyridine (DMAP), diisopropylethylamine, pyridine, triethylamine, KOH, potassium t-butoxide and NaOH etc. to catalyze the reaction by deprotonation of the indole nitrogen atom and to neutralize any acids generated, and at a temperature from 0° C. up to about 22° C. (room temperature).

Regardless of the synthesis selected, some of the preferred compounds which result from the synthetic techniques described herein include:

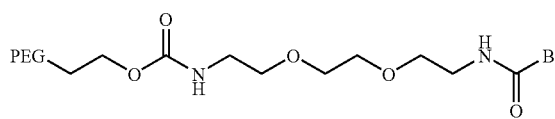

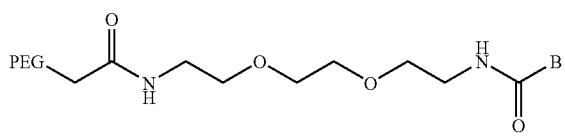

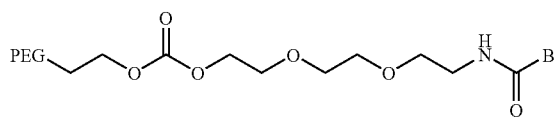

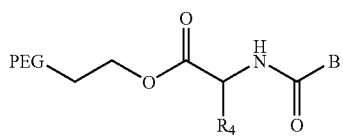

-continued

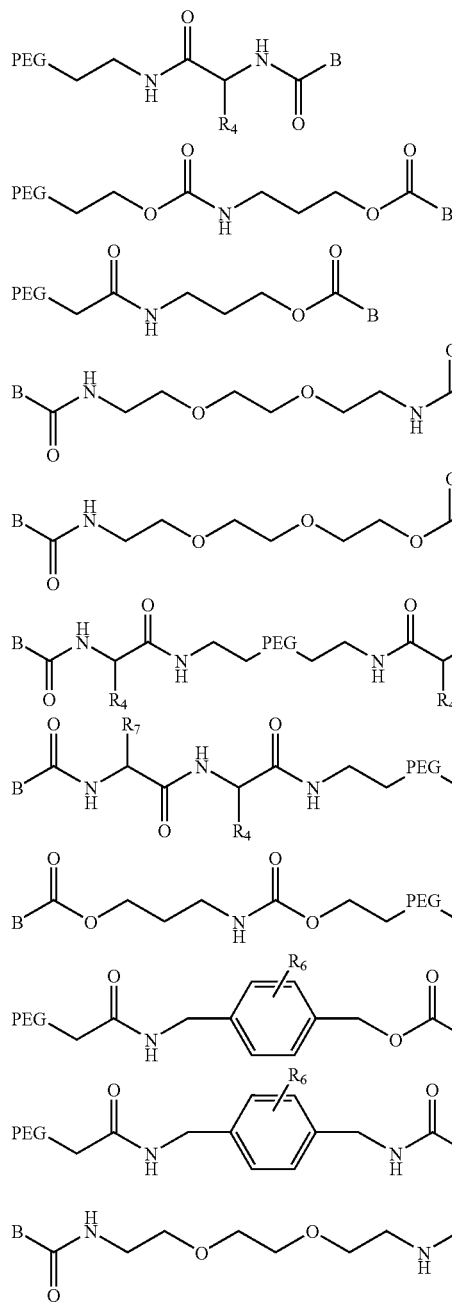
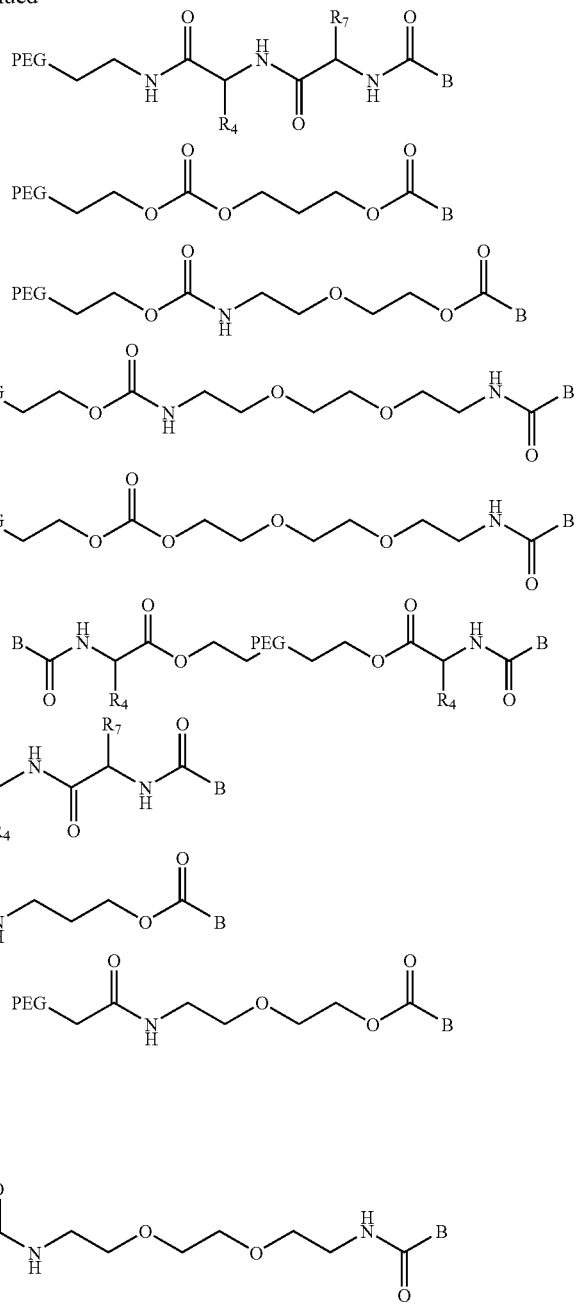

where all variables are as previously defined.

Methods of Treatment

Another aspect of the present invention provides methods of treatment for various medical conditions in mammals. The methods include administering to the mammal in need of such treatment, an effective amount of a prodrug, such as, a 9-nitro-paullone-PEG conjugate, which has been prepared as described herein. The compositions are useful for, among other things, treating neoplastic disease, reducing tumor burden, preventing metastasis of neoplasms and preventing recurrences of tumor/neoplastic growths in mammals.

The amount of the prodrug administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, paullone prodrugs are administered in amounts ranging from about 10 to about 30 mg/kg per day, based on the amount of the paullone moiety. Alsterpaullone prodrugs are also administered in amounts ranging from about 12 to about 20 mg/kg per day. Preferably, alsterpaullone prodrugs are administered in amounts ranging from about 12 to about 18 mg/kg per day. The range set forth above is illustrative and those skilled in the art will determine the optimal dosing of the prodrug selected based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof.

EXAMPLES

The following examples serve to provide further appreciation of the invention but are not meant in any way to restrict the effective scope of the invention. The underlined and bold-faced numbers recited in the Examples correspond to those shown in the Figures.

General Procedures. Alsterpaullone (9-nitro paullone) 1 was provided by the National Cancer Institute and used without further purification. All reactions were run under an atmosphere of dry nitrogen or argon. Commercial reagents were used without further purification. All PEG compounds were dried under vacuum or by azeotropic distillation from toluene prior to use. NMR spectra were obtained using a Varian Mercury® 300 NMR spectrometer and deuterated chloroform or methanol as the solvents unless otherwise specified. Chemical shifts ($\delta$) are reported in parts per million (ppm) downfield from tetramethylsilane (TMS).

HPLC method. The reaction mixtures and the purity of intermediates and final products were monitored by a Beckman Coulter System Gold® HPLC instrument employing a ZOBAX® 300 SB C8 reversed phase column (150×4.6 mm) or a Phenomenex Jupiter® 300A C18 reversed phase column (150×4.6 mm) with a multi avelength UV detector (main wavelength used 280 nm), using a gradient of 5-80% of acetonitrile in 0.5% trifluoroacetic acid (TFA) at a flow rate of 1 mL/min.

Example 1

Compound 3. To a solution of di-tert-butyl dicarbonate (15 g, 0.086 mol) in 1,4-dioxane (150 mL) cooled to 5° C. in an ice bath was added a solution of 2,2'-(ethylenedioxy)bis (ethylamine) (25.85 g, 174.4 mmol) in 1,4-dioxane (100 mL) dropwise over a period of 1 hr. The reaction mixture was allowed to warm to room temperature and stirred for two more hours. The solvent was removed under reduced pressure and the residue dissolved in methylene chloride (DCM, 150 mL), washed with water (3×150 mL), dried over magnesium sulfate ($MgSO_4$) filtered, and the solvent evaporated under reduced pressure to yield 3 (13.84 g, mmol, 80%). $^{13}$C NMR (75.5 MHz, $CDCl_3$) $\delta$28.39, 40.31, 70.12, 73.45, 79.03, 115.76.

Example 2

Compound 4. To a suspension of alsterpaullone 1 (1.5 g, 5.11 mmol) in anhydrous tetrahydrofuran (THF, 600 mL) was added 4-nitrophenyl chloroformate (3.082 g, 15.29 mmol) and 4-dimethylaminopyridine (DMAP, 3.736 g, 30.57 mmol) and the reaction mixture stirred at room temperature for 2 hrs. Compound 3 (12.54 g, 50.97 mmol) was added and the mixture stirred at room temperature for an additional 12 hrs. The solvent was removed under reduced pressure, the residue dissolved in DCM (300 mL), filtered, washed with 0.25 N HCl (3×300 mL). The organic layer was dried ($MgSO_4$), filtered, and the solvent removed under reduced pressure. The residue was further purified by column chromatography to yield 4 (1.18 g, 2.08 mmol, 40.6%). $^{13}$C NMR (75.5 MHz, $CDCl_3$) $\delta$28.36, 29.74, 31.56, 40.12, 40.96, 68.92, 69.99, 70.30, 79.51, 113.89, 115.05, 116.92, 119.87, 121.69, 123.03, 124.42, 126.44, 129.10, 129.62, 133.92, 135.55, 140.88, 143.37, 150.83, 155.88, 172.94.

Example 3

Compound 5. To a mixture of trifluoroacetic acid (TFA, 0.2 mL) and anhydrous DCM (1.8 mL) was added 4 (0.10 mg, 0.176 mmol) and the reaction mixture was stirred for 45 minutes at room temperature. The solvents were removed under reduced pressure and the residue washed with ethyl ether to give 5 (0.102 g, 0.176 mmol, 99%). $^{13}$C NMR (75.5 MHz, $CDCl_3$/DMSO-$d_6$) $\delta$30.42, 38.75, 39.96, 65.96, 68.32, 69.28, 69.49, 112.11, 114.35, 115.22, 118.44, 121.42, 122.32, 123.63, 125.78, 127.66, 128.61, 134.44, 135.03, 139.93, 142.53, 151.21, 172.44.

Example 4

Compound 7. To a solution of 5 (0.102 g, 0.176 mmol) in anhydrous dimethylformamide (DMF, 3 mL) and DCM (37 mL) was added BSC-PEG linker 6 (2.36 g, 0.059 mmol) and DMAP (0.022 g, 0.176 mmol). The reaction was stirred at room temperature for 12 hrs, the solution concentrated under reduced pressure, and the PEG derivative precipitated with ethyl ether (150 mL). The crude product was crystallized from isopropanol (IPA, 200 mL) to give 7 (2.0 g, 0.0488 mmol, 87%). $^{13}$C NMR (75.5 MHz, $CDCl_3$) $\delta$31.24, 40.17, 40.52, 63.52, 68.56, 69.00, 70.10-74.00(PEG), 113.25, 114.64, 116.26, 119.17, 121.28, 122.91, 123.68, 126.00, 128.42, 128.94, 135.43, 140.30, 142.83, 150.46, 155.94, 171.64.

Example 5

Compound 9. To a solution of 5 (0.765 g, 1.64 mmol) in anhydrous DMF (20 mL) and DCM (90 mL) was added PEG diacid 8 (7.5 g, 0.37 mmol), 1-[3-(dimethylamino)-propyl]-3-ethylcarbodiimide hydrochloride (EDC, 0.315 g 1.64 mmol), and DMAP (0.364 g, 2.98 mmol), and stirred at room temperature for 12 hrs. The solvent was removed under reduced pressure and the residue crystallized from IPA (200 mL) to give 9 (7.2 g, 0.343 mmol, 93%). $^{13}$C NMR (75.5 MHz, $CDCl_3$) $\delta$31.22, 37.97, 40.47, 68.50-74.00 (PEG), 113.27, 114.58, 116.24, 119.10, 121.19, 122.91, 123.57, 125.98, 128.38, 128.90, 133.78, 135.49, 140.30, 142.77, 150.39, 169.76, 171.62.

Example 6

Compound 13. A). To a solution of tert-butyl N-(3-hydroxypropyl)-carbamate (5.0 g, 28.57 mmol), N,N'-disuccinimidyl carbonate (DSC, 9.6 g, 37.5 mmol) in chloroform (125 mL) was added pyridine (2.99 mL, 37.02 mmol) and the reaction mixture stirred at room temperature for 12 hrs. The mixture was washed with 0.5 N HCl (60 mL), dried (MgSO$_4$), filtered, and solvent removed under reduced pressure to give compound 12 (8.2 g, 25.92 mmol, 90.7%). $^{13}$C NMR (75.5 MHz, CDCl$_3$) δ25.46, 28.36, 28.91, 36.80, 68.91, 79.35, 151.40, 155.76, 168.50. B). To a reaction mixture of 1 (0.25 g, 0.85 mmol) and potassium hydroxide (KOH, 0.114 g, 2.03 mmol) in DMF/THF (20 mL/100 mL) stirred for 1 hr at 0° C. in an ice-salt bath was added 12 (0.805 g, 2.55 mmol) and the resulting reaction mixture was gradually warmed to room temperature and stirred for 24 hrs. The solvent was removed under reduced pressure, the residue dissolved in DCM (100 mL), filtered, washed with 0.25 N HCl (2×200 mL). The organic layer was dried (MgSO$_4$), filtered, and the solvent removed under reduced pressure. The residue was further purified by column chromatography to yield 13 (0.340 g, 0.706 mmol, 83%). $^{13}$C NMR (75.5 MHz, CDCl$_3$) δ25.68, 28.43, 28.95, 31.36, 37.00, 65.53, 67.97, 76.57, 79.56, 114.83, 115.83, 119.35, 120.68, 122.82, 123.89, 127.95, 128.24, 129.87, 134.65, 141.06, 144.30, 150.77, 155.62, 172.72.

Example 7

Compound 14. To a solution of 13 (0.146 g, 0.295 mmol) in DCM (3 mL) cooled to 0° C. using an ice-salt bath was added TFA (3 mL) drop wise over 1 hr with stirring. The solvents were removed under reduced pressure to give 14 (0.146 g, 0.295 mmol, ~100%).

Example 8

Compound 15. To a solution of 14 (0.146 g, 0.295 mmol) in anhydrous DMF/DCM (6 mL/9 mL) was added PEG linker 6 (2.98 g, 0.074 mmol) and DMAP (0.072 g, 0.59 mmol). The reaction mixture was stirred at room temperature for 12 hrs, diluted with DCM, washed with 0.1 N HCl (2×20 mL) and brine (20 mL). Removal of the solvent under reduced pressure gave crude product which was crystallized from DMF/ethanol (45 mL/45 mL) to give 14 (2.5 g, 0.0612 mmol, 83%). $^{13}$C NMR (75.5 MHz, CDCl$_3$) δ28.08, 31.36, 38.63, 63.69, 67.05, 69.35, 69.92, 70.12, 70.30-73.50 (PEG), 114.56, 115.42, 119.25, 120.36, 123.11, 123.23, 127.65, 128.95, 129.34, 135.32, 140.85, 144.01, 150.36, 155.61, 171.83.

Example 9

Compound 16. A solution of 14 (0.457 g, 0.922 mmol) and 8 (4.6 g, 0.23 mmol) in anhydrous DMF (30 mL) and DCM (46 mL) was cooled to 0° C. EDC (0.177 g, 0.922 mmol) and DMAP (0.562 g, 4.6 mmol) were added all at once and the reaction mixture stirred at room temperature for 12 hrs. The solution was washed by 0.1 N HCl (2×30 mL) and brine (30 mL), dried (MgSO$_4$), filtered, the solvent removed under reduced pressure, and the residue crystallized from IPA (100 mL) to give 16 (4.26 g, 0.205 mmol, 89%). $^{13}$C NMR (75.5 MHz, CDCl$_3$) δ28.08, 31.12, 34.86, 65.20, 68.50-73.50 (PEG), 114.37, 115.43, 118.90, 120.09, 122.68, 123.14, 127.54, 128.71, 129.37, 134.79, 135.29, 140.57, 143.79, 150.28, 169.59, 171.83.

Examples 10-13

Compound 17. The process of Examples 1-4 are repeated except that an equimolar amount of terguride is used in place of alsterpaullone 1.

Examples 14-16

Compound 18. The processes of Examples 5-7 are repeated except that an equimolar amount of kenpaullone is used in place of alsterpaullone 1.

Example 17

In this example, in vitro data is presented for compounds 7, 9, 15 and 16.

In Vitro Bioassay

A series of in vitro assays were conducted to determine the IC$_{50}$ for unmodified alsterpaullone, compound 7 and compound 12 using die P388/O (murine lymphoid neoplasm, Southern Research Institute) cell line. The P388/0 cells were grown in RPMI-1640 medium (Whittaker Bioproducts, Walkersville, Md.)+10% FBS (Hyclone Inc., Logan Utah). Bioassays were performed in their respective media containing antibiotics.

The PEG-alsterpaullone derivatives were dissolved in water and diluted to the appropriate concentrations in culture media.

The assays were performed in duplicate in 96-well microtiter cell culture plates. Two fold serial dilution of the compounds were done in the microtiter plates. Cells were detached by incubating with Trypsin-EDTA (0.05% Trypsin, 0.53 mM EDTA; GIBCOBRL(Life Technologies)) at 37°. Trypsin was inactivated by adding the appropriate media for each cell line containing 10% FBS. To each well of the microtiter plates, 10,000 cells were added. After three days, cell growth was measured by addition of a metabolic indicator dye according to the manufacturer's protocol (Promega). The IC$_{50}$ value for the test compounds are provided in Table 1 below.

TABLE 1

Properties of PEG Alsterpaullone derivatives

| Compound | MW | $t_{1/2}$ (PBS buffer, h) | $t_{1/2}$ (rat plasma, h) | % Active | Solubility of PEG conjugates (mg/mL) | Solubility of alsterpaullone in conjugates (mg/mL) |
| --- | --- | --- | --- | --- | --- | --- |
| 7 | 40988 | 38.5 h | 0.42 | 1.44 | 153 | 2.20 |
| 9 | 21012 | 35 h | 1.3 | 2.80 | 189 | 5.30 |
| 15 | 40842 | 1732 h | 12 | 1.44 | 172 | 2.48 |
| 16 | 20754 | 1155 h | 58 | 2.88 | 186 | 5.36 |

While there have been described what are presently believed to be the preferred embodiments of the invention,

What is claimed is:

1. A compound of the formula:

$$B-(C(Y_1))_p-L_1-R_1-L_1-(C(Y_1))_p-B$$

wherein:
$R_1$ is a polyalkylene oxide;
$Y_1$ is O, S or $NR_2$;
$R_2$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
$L_1$ is a bifunctional linker selected from the group consisting of —NH(CH$_2$CH$_2$O)$_n$(CH$_2$)$_n$NR$_3$—, —NH(CH$_2$CH$_2$O)$_n$C(O)—, —NH(CR$_4$R$_5$)$_n$OC(O)—, —C(O)(CR$_4$R$_5$)$_n$NHC(O)(CR$_8$R$_7$)$_q$NR$_3$—, —C(O)O(CH$_2$)$_n$O—, —C(O)(CR$_4$R$_5$)$_n$NR$_3$—, —C(O)NH(CH$_2$CH$_2$O)$_n$(CH$_2$)$_n$NR$_3$—, —C(O)O⁻(CH$_2$CH$_2$O)$_n$NR$_3$—, —C(O)NH(CR$_4$R$_5$)$_n$O—, —C(O)O(CR$_4$R$_5$)$_n$O—, —C(O)NH(CH$_2$CH$_2$O)$_n$—, —NH(CR$_4$R$_5$)$_n$—⟨phenyl-R$_6$⟩—(CR$_8$R$_7$)$_q$OC(O)—, and —NH(CR$_4$R$_5$)$_n$—⟨phenyl-R$_6$⟩—(CR$_8$R$_7$)$_q$NR$_3$C(O)—, wherein
$R_3$, $R_4$, $R_5$, $R_7$, and $R_8$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
$R_6$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $NO_2$, haloalkyl and halogen; and n and q are each a positive integer;
p is 0 or 1; and
B is

[structure of fused ring system with rings A, B, C, D bearing substituents $R_{1'}$, $R_{2'}$, $R_{3'}$, $R_{4'}$, $R_{5'}$, $R_{7'}$, $R_{8'}$, $R_{9'}$, $R_{10'}$, $R_{11'}$, and $Y_2$]

wherein
$Y_7$ is O, S or $NR_{12'}$; and
$R_{1'}$-$R_{12'}$ are each independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-12}$ alkenyls, $C_{3-12}$ substituted alkenyls, $C_{3-12}$ alkynyls, $C_{3-12}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy, halo-, nitro-, cyano-, hydroxyl-, amino-, carboxy- and trifluoromethyl, (i) wherein the substituted alkyls, substituted cycloalkyls, substituted aryls and substituted heteroalkyls are independently substituted with the group consisting of halo, alkoxy, nitro, carboxy, amino, alkylamino, hydroxyl and mercapto; and (ii) wherein a carbon of the heteroalkyls and heteroalkoxy is independently substituted with the group consisting of O, N and S.

2. A compound of claim 1, wherein $Y_1$ is O.

3. The compound of claim 1 wherein $R_2$ is selected from the group consisting of hydrogen, methyl and ethyl.

4. The compound of claim 3 wherein $R_2$ is hydrogen.

5. The compound of claim 1 wherein said paullone is a member of the group consisting of alsterpaullone and kenpaullone.

6. The compound of claim 1, wherein $R_1$ is a polyethylene glycol.

7. The compound of claim 6, wherein $R_1$ is selected from the group consisting of —O—C(O)CH$_2$—O—(CH$_2$CH$_2$O)$_x$—CH$_2$C(O)—)—, —NR$_3$CH$_2$CH$_2$—O—(CH$_2$CH$_2$O)$_x$—CH$_2$CH$_2$NR$_3$—, —SHCH$_2$CH$_2$—O—(CH$_2$CH$_2$O)$_x$—CH$_2$CH$_2$SH—, wherein
x is the degree of polymerization; and
$R_3$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, (i) wherein the substituted alkyls, substituted cycloalkyls, substituted aryls and substituted heteroalkyls are independently substituted with the group consisting of halo, alkoxy, nitro, carboxy, amino, alkylamino, hydroxyl and mercapto; and (ii) wherein a carbon of the heteroalkyls and heteroalkoxy is independently substituted with the group consisting of O, N and S.

8. The compound of claim 1, wherein $R_1$ is —O—$(CH_2CH_2O)_x$— and x is a positive integer so that the weight average molecular weight is at least about 20,000 Da.

9. The compound of claim 1, wherein $R_1$ has a weight average molecular weight of from about 20,000 Da to about 100,000 Da.

10. The compound of claim 1, wherein $R_1$ has a weight average molecular weight of from about 25,000 Da to about 60,000 Da.

11. A compound of claim 1, selected from the group consisting of:

B is

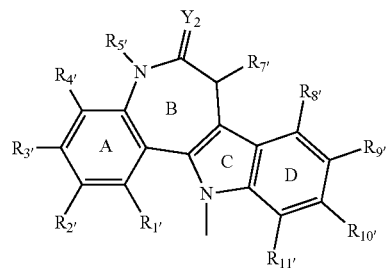

$Y_2$ is O, S or $NR_{12'}$;

$R_{1'}$-$R_{12'}$ are each independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-12}$ alkenyls, $C_{3-12}$ substituted alkenyls, $C_{3-12}$ alkynyls, $C_{3-12}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$

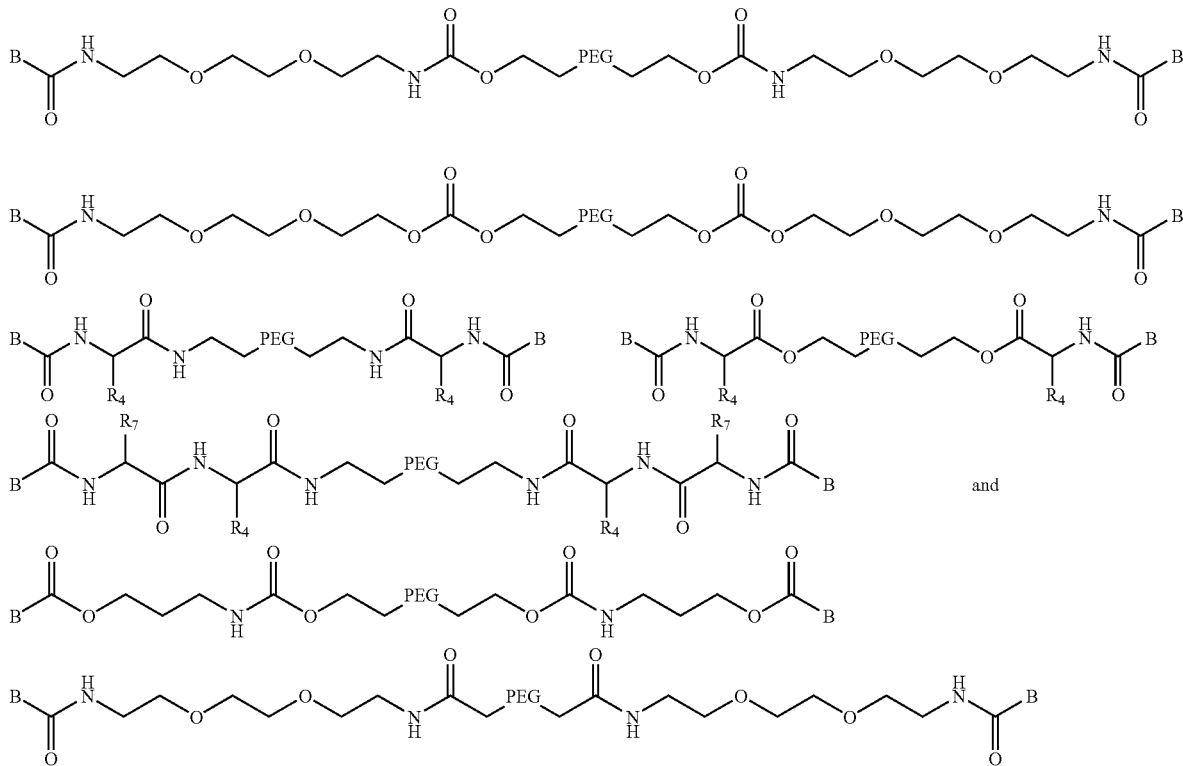

wherein:

PEG is —O(—$CH_2CH_2O)_x$—;

x is the degree of polymerization;

$R_4$, $R_5$ and $R_6$ are independently selected from the group consisting of is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

heteroalkoxy, halo-, nitro-, cyano-, hydroxyl-, amino-, carboxy- and trifluormethyl, (i) wherein the substituted alkyls, substituted cycloalkyls, substituted aryls and substituted heteroalkyls are independently substituted with the group consisting of halo, alkoxy, nitro, carboxy, amino, alkylamino, hydroxyl and mercapto; and (ii) wherein a carbon of the heteroalkyls and heteroalkoxy is independently substituted with the group consisting of O, N and S.

12. A compound of claim 11 wherein said paullone is a member of the group consisting of alsterpaullone and kenpaullone.

13. A method of preparing a polymer conjugate of the formula:

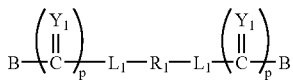

wherein

R$_1$ is a polyalkylene oxide;

L$_1$ is a bifunctional spacer selected from the group consisting of

—NH(CH$_2$CH$_2$O)$_n$(CH$_2$)$_n$NR$_3$—,

—NH(CH$_2$CH$_2$O)$_n$C(O)—,

—NH(CR$_4$R$_5$)$_n$NHC(O)(CR$_8$R$_7$)$_q$NR$_3$—,

—C(O)(CR$_4$R$_5$)$_n$NHC(O)(CR$_8$R$_7$)$_n$NR$_3$—,

—C(O)O(CH$_2$)$_n$O—,

—C(O)(CR$_4$R$_5$)$_n$NR$_3$—,

—C(O)NH(CH$_2$CH$_2$O)$_n$(CH$_2$)$_n$NR$_3$—,

—C(O)O⁻(CH$_2$CH$_2$O)$_n$NR$_3$—,

—C(O)NH(CR$_4$R$_5$)$_n$O—,

—C(O)O(CR$_4$R$_5$)$_n$O—,

—C(O)NH(CH$_2$CH$_2$O)$_n$—,

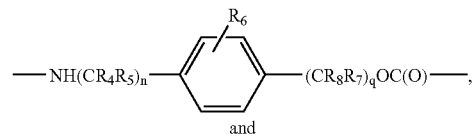

and

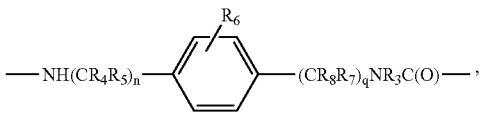

wherein

R$_3$, R$_4$, R$_5$, R$_7$, and R$_8$ are independently selected from the group consisting of hydrogen, C$_{1-6}$alkyls, C$_{3-12}$ branched alkyls, C$_{3-8}$cycloalkyls, C$_{1-6}$substituted alkyls, C$_{3-8}$substituted cycloalkyls, aryls substituted aryls, aralkyls, C$_{1-6}$ heteroalkyls, substituted C$_{1-6}$heteroalkyls, C$_{1-6}$alkoxy, phenoxy and C$_{1-6}$heteroalkoxy;

R$_6$ is selected from the group consisting of hydrogen, C$_{1-6}$alkyls, C$_{3-12}$ branched alkyls, C$_{3-8}$ cycloalkyls, C$_{1-6}$ substituted alkyls, C$_{3-8}$ substituted cycloalkyls, aryls substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy, NO$_2$, haloalkyl and halogen; and n and q are each a positive integer;

Y$_1$ is O, S or NR$_2$;

R$_2$ is selected from the group consisting of hydrogen, C$_{1-6}$alkyls, C$_{3-12}$ branched alkyls, C$_{3-8}$cycloalkyls, C$_{1-6}$substituted alkyls, C$_{3-8}$ substituted cycloalkyls, aryls substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy;

p is 0 or 1; and

B is

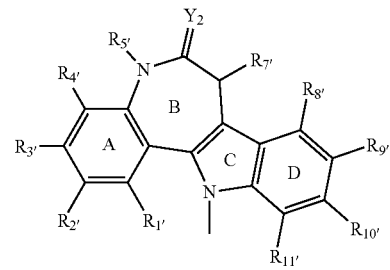

wherein

Y$_2$ is O, S or NR$_{12}$; and

R$_{1'}$-R$_{12'}$ are each independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-12}$ alkenyls, C$_{3-12}$ substituted alkenyls, C$_{3-12}$ alkynyls, C$_{3-12}$ substituted alkynyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy, C$_{1-6}$ heteroalkoxy, halo-, nitro-, cyano-, hydroxyl-, amino-, carboxy- and trifluormethyl, (i) wherein the substituted alkyls, substituted cycloalkyls, substituted aryls and substituted heteroalkyls are independently substituted with the group consisting of halo, alkoxy, nitro, carboxy, amino, alkylamino, hydroxyl and mercapto; and (ii) wherein a carbon of the heteroalkyls and heteroalkoxy is independently substituted with the group consisting of O, N and S;

comprising:

a) acylating a paullone, b) attaching a blocked bifunctional spacer to form a blocked intermediate, and c) deblocking said blocked intermediate and reacting the deblocked intermediate with an activated polymer under conditions sufficient to cause a polymeric conjugate to be formed.

14. A method of preparing a polymer conjugate of the formula:

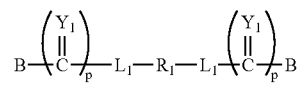

wherein:

R$_1$ is a polyalkylene oxide;

L$_1$ is a bifunctional spacer selected from the group consisting of

—NH(CH$_2$CH$_2$O)$_n$(CH$_2$)$_n$NR$_3$—,

—NH(CH$_2$CH$_2$O)$_n$C(O)—, —NH(CR$_4$R$_5$)$_n$OC(O)—,

—C(O)(CR$_4$R$_5$)$_n$NHC(O)(CR$_8$R$_7$)$_q$NR$_3$—,

—C(O)O(CH$_2$)$_n$O—,

—C(O)(CR$_4$R$_5$)$_n$NR$_3$—,

—C(O)NH(CH$_2$CH$_2$O)$_n$(CH$_2$)$_n$NR$_3$—,

—C(O)O—(CH$_2$CH$_2$O)$_n$NR$_3$—,

—C(O)NH(CR$_4$R$_5$)$_n$)—,

—C(O)NH(CH$_2$CH$_2$O)$_n$—,

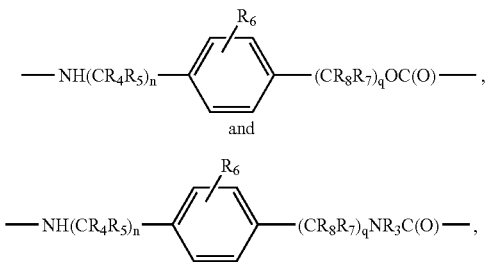

and wherein
R$_3$, R$_4$, R$_5$, R$_7$, and R$_8$ are independently selected from the group consisting of hydrogen, C$_{1-6}$alkyls, C$_{3-12}$ branched alkyls, C$_{3-8}$cycloalkyls, C$_{1-6}$substituted alkyls, C$_{3-8}$substituted cyloalkyls, aryls substituted aryls, aralkyls, C$_{1-6}$ heteroalkyls, substituted C$_{1-6}$heteroalkyls, C$_{1-6}$alkoxy, phenoxy and C$_{1-6}$heteroalkoxy;

R$_6$ is selected from the group consisting of hydrogen, C$_{1-6}$alkyls, C$_{3-12}$ branched alkyls, C$_{3-8}$ cycloalkyls, C$_{1-6}$ substituted alkyls, C$_{3-8}$ substituted cycloalkyls, aryls substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy, NO$_2$, haloalkyl and halogen; and n and q are each a positive integer;

Y$_1$ is O, S or NR$_2$;

R$_2$ is selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy;

p is 0 or 1; and
B is

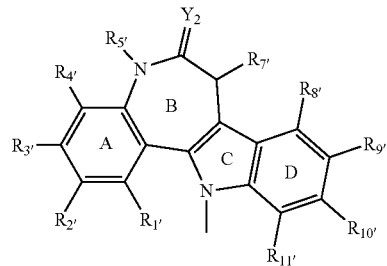

wherein

Y$_2$ is O, S or NR$_{12'}$; and

R$_1$,-R$_{12}$, are each independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-12}$ alkenyls, C$_{3-12}$ substituted alkenyls, C$_{3-12}$ alkynyls, C$_{3-12}$ substituted alkynyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy, C$_{1-6}$ heteroalkoxy, halo, nitro-, cyano-, hydroxyl-, amino-, carboxy- and trifluoromethyl, (i) wherein the substituted alkyls, substituted cycloalkyls, substituted aryls and substituted heteroalkyls are independently substituted with the group consisting of halo, alkoxy, nitro, carboxy, amino, alkylamino, hydroxyl and mercapto; and (ii) wherein a carbon of the heteroalkyls and heteroalkoxy is independently substituted with the group consisting of O, N and S;

comprising:

a) deprotonating a paullone, b) attaching a blocked bifunctional spacer to form a blocked intermediate, and c) deblocking said blocked intermediate and reacting the deblocked intermediate with an activated polymer under conditions sufficient to cause a polymeric conjugate to be formed.

* * * * *

UNITED STATES PATENT AND TRADEMARK OFFICE
CERTIFICATE OF CORRECTION

| | | |
|---|---|---|
| PATENT NO. | : 7,393,953 B2 | |
| APPLICATION NO. | : 10/403789 | |
| DATED | : July 1, 2008 | |
| INVENTOR(S) | : Hong Zhao et al. | |

It is certified that error appears in the above-identified patent and that said Letters Patent is hereby corrected as shown below:

Column 23, line 62 in claim 1,

"aryls substituted" should read -- aryls, substituted --.

Column 24, line 2 in claim 1,

"aryls substituted" should read -- aryls, substituted --.

Column 24, line 49 in claim 5,

"said paullone" should read -- B --.

Column 24, line 56-57 in claim 7, the chemical formula

"-O-C(O)CH$_2$-O-(CH$_2$CH$_2$O$_x$-CH$_2$C(O)-)-," should appear as follows:

-- -O-C(O)CH$_2$-O-(CH$_2$CH$_2$O)$_x$-CH$_2$C(O)-O-, --.

Column 24, line 67 in claim 7,

"aryls substi-" should read -- aryls, substi- --.

Column 25, line 65 in claim 11,

"aryls substituted" should read -- aryls, substituted --.

Column 27, line 1 in claim 12,

"said paullone" should read -- B --.

Column 27, line 22 in claim 13, the chemical formula

"-NH(CR$_4$R$_5$)$_n$NHC(O)(CR$_8$R$_7$)$_q$NR$_3$-," should appear as follows:

-- -NH(CR$_4$R$_5$)$_n$OC(O)-, --.

UNITED STATES PATENT AND TRADEMARK OFFICE
CERTIFICATE OF CORRECTION

PATENT NO. : 7,393,953 B2
APPLICATION NO. : 10/403789
DATED : July 1, 2008
INVENTOR(S) : Hong Zhao et al.

It is certified that error appears in the above-identified patent and that said Letters Patent is hereby corrected as shown below:

Column 27, line 24 in claim 13, the chemical formula

"-C(O)(CR$_4$R$_5$)$_n$NHC(O)(CR$_8$R$_7$)$_n$NR$_3$-," should appear as follows:

-- -C(O)(CR$_4$R$_5$)$_n$NHC(O)(CR$_8$R$_7$)$_q$NR$_3$-, --.

Column 27, line 63 in claim 13,

"aryls substituted" should read -- aryls, substituted --.

Column 28, line 5 in claim 13,

"aryls substituted" should read -- aryls, substituted --.

Column 29, line 10 in claim 14, the chemical formula

"-C(O)NH(CR$_4$R$_5$)$_n$-," should appear as follows:

-- -C(O)NH(CR$_4$R$_5$)$_n$O-,

-C(O)O(CR$_4$R$_5$)$_n$O-, --.

Signed and Sealed this

Fourteenth Day of October, 2008

JON W. DUDAS
*Director of the United States Patent and Trademark Office*